(12) United States Patent
Filippo

(10) Patent No.: US 7,726,809 B2
(45) Date of Patent: Jun. 1, 2010

(54) CONTACT LENS, METHOD FOR PRODUCING SAME, AND PACK FOR STORAGE AND MAINTENANCE OF A CONTACT LENS

(75) Inventor: Alessandro Filippo, Azzano Decimo (IT)

(73) Assignee: Safilens S.R.L., Staranzano (IT)

( * ) Notice: Subject to any disclaimer, the term of this patent is extended or adjusted under 35 U.S.C. 154(b) by 81 days.

(21) Appl. No.: 11/814,556

(22) PCT Filed: Feb. 9, 2006

(86) PCT No.: PCT/IT2006/000067
§ 371 (c)(1),
(2), (4) Date: Jul. 23, 2007

(87) PCT Pub. No.: WO2006/085351
PCT Pub. Date: Aug. 17, 2006

(65) Prior Publication Data
US 2008/0170201 A1 Jul. 17, 2008

(30) Foreign Application Priority Data
Feb. 9, 2005 (IT) ............ PD2005A0030
Jun. 24, 2005 (IT) ............ PD2005A0190

(51) Int. Cl.
*G02C 7/04* (2006.01)
(52) U.S. Cl. .............. 351/160 H; 351/177; 422/41; 424/488
(58) Field of Classification Search ........... 351/160 H
See application file for complete search history.

(56) References Cited

U.S. PATENT DOCUMENTS

| 4,264,155 | A | * | 4/1981 | Miyata ............ 351/160 H |
| 4,668,506 | A | | 5/1987 | Bawa |
| 5,106,615 | A | | 4/1992 | Dikstein |
| 5,508,317 | A | | 4/1996 | Muller |
| 5,587,175 | A | * | 12/1996 | Viegas et al. ........... 424/427 |
| 5,770,628 | A | | 6/1998 | Cantoro |
| 5,939,466 | A | | 8/1999 | Bachmann et al. |
| 6,056,950 | A | | 5/2000 | Saettone et al. |
| 6,143,210 | A | | 11/2000 | Wrue et al. |

(Continued)

FOREIGN PATENT DOCUMENTS

EP 1 247 532 10/2002

(Continued)

OTHER PUBLICATIONS

"Development of a Simple Dry Eye Model in the Albino Rabbit and Evaluation of Some Tear Substitutes" by Burgalassi, et al., published in Ophthalanic Res, 1999, 3 I, pp. 229-235.

(Continued)

*Primary Examiner*—Jessica T Stultz
(74) *Attorney, Agent, or Firm*—Gottlieb, Rackman & Reisman, P.C.

(57) ABSTRACT

A contact lens (4) comprises a solid component capable of imparting shape and structure to said lens, and a liquid component, at least partially contained in the solid component, capable of favoring the compatibility between said lens and the eye of a user of said lens, wherein the liquid component comprises a solution capable of being used as a lachrymal substitute.

21 Claims, 1 Drawing Sheet

U.S. PATENT DOCUMENTS

| | | | |
|---|---|---|---|
| 6,277,365 B1 * | 8/2001 | Ellis et al. | 424/78.04 |
| 6,410,045 B1 | 6/2002 | Schultz et al. | |
| 6,429,194 B1 | 8/2002 | Leahy et al. | |
| 2004/0214914 A1 | 10/2004 | Marmo | |
| 2005/0014691 A1 | 1/2005 | Bakhit et al. | |
| 2006/0094643 A1 * | 5/2006 | Svirkin et al. | 514/8 |
| 2008/0307751 A1 * | 12/2008 | Newman et al. | 53/425 |

FOREIGN PATENT DOCUMENTS

| | | |
|---|---|---|
| FR | 2 358 896 | 2/1978 |
| WO | WO 98/04934 | 3/1998 |
| WO | 98/30248 | 7/1998 |
| WO | 98/55155 | 12/1998 |
| WO | WO 99/13663 | 3/1999 |
| WO | WO 01/82984 | 11/2001 |
| WO | 02/060495 | 8/2002 |
| WO | 2006/040130 | 10/2004 |
| WO | 2005/025991 | 3/2005 |
| WO | 2006/038080 | 4/2006 |

OTHER PUBLICATIONS

"Selbstmedikationsliste", Deutscher Apotheker Verlag 2002, pp. 375-378.

"Contact lens: a textbook for practitioner and student", third edition (1989), p. 982.

* cited by examiner

CONTACT LENS, METHOD FOR PRODUCING SAME, AND PACK FOR STORAGE AND MAINTENANCE OF A CONTACT LENS

TECHNICAL FIELD

The present invention relates to a contact lens, having the characteristics listed in the preamble of the main claim. It also concerns a method for producing a contact lens, according to what is stated in the claims, a liquid for preserving contact lenses according to the claims and also a pack for the storage and maintenance of a soft contact lens having the characteristics listed in the claims.

TECHNOLOGICAL BACKGROUND

It is known that contact lenses, whether they are cosmetic or corrective, are widely used among the population. Among these, particular importance is given to contact lenses of the soft type, which, compared with the other types of lenses (rigid or semi-rigid) provide greater comfort in use.

This advantageous characteristic is provided by the high hydrophilic capacity of the lens which, containing a substantial percentage of water, permits greater compatibility between the lens and the eye, in addition to a greater deformability of the lens which allows it to adapt better to the surface of the eye.

Soft contact lenses are conventionally produced by means of a method which provides for a first step of obtaining a dry semi-manufactured product of lenticular shape and made of polymeric material, which may in turn be obtained by the polymerization of a monomer directly in a die (moulding technique), or by turning a disc of already polymerized material (turning technique).

Independently of the technique used for its preparation, the dry semi-manufactured product is then hydrated by immersion in a saline solution (known as a physiological solution) composed of around 1% by weight of sodium chloride in water. The polymeric material used is typically endowed with optimum hydrophilic properties, and is normally a polymeric mixture based on HEMA, so that a substantial amount of saline solution, between 25% and 75%, is absorbed in the dry semi-manufactured product.

The absorption of the liquid component, besides imparting to the lens the above-mentioned characteristics of compatibility and softness, also includes physical expansion of the dry semi-manufactured product, both radial and linear, thus determining both the final dimensions of the contact lens, and its optical properties.

The contact lens thus obtained thus comprises a solid component, defining the structural portion of the lens and composed of the polymeric material, and also a liquid component, composed of the saline solution, distributed almost uniformly in the solid component.

The marketing of the contact lens provides for the preparation of suitable packs, produced for example in the form of blister packs, in which the lenses are stored and maintained for the entire period between the end of the process of manufacturing same, and the first use thereof by a user.

The packs must therefore be arranged to maintain unaltered over time the mechanical, optical and dimensional characteristics of the lenses.

To this end, the packs typically comprise a support defining a container which is filled, at least partially, with physiological solution, in which the contact lens, in its turn, is immersed. The container is further conveniently closed by a membrane, generally constituted by a thin metallic sheet (known in the field as a "foil"), subsequently removable by the user in order to extract the lens from the container.

It is known that one of the major drawbacks arising from the use of contact lenses is represented by the sensation of ocular dryness, caused by the reduction or by the breakdown of the lachrymal film which surrounds and protects the cornea. This typically involves a sensation of discomfort and irritation which frequently forces the user to remove the lenses and which, in the long term, may also lead to changes in the lachrymal function and to other pathological disfunctions at the expense of the eye (such as, for example, corneal or conjunctival inflammation).

Also owing to this drawback, many persons are capable of wearing the contact lenses only for a very limited time or are even prevented from doing so.

In order to overcome this drawback, at least in part, various technical solutions have been developed and proposed.

A first of these solutions, for the formation of the solid component, provides for the use of polymers and/or copolymers having the highest possible hydrophilic properties. Such polymers and/or copolymers may be used for producing the entire solid component of the lens, or only as an outer coating of same. The use of such polymers, however, has a negative effect on the overall costs of production, but without succeeding in providing resolutory advantages with regard to the above-mentioned drawback. Moreover, such use may also turn out to be counter-productive in the case where the lens remains in the eye for a prolonged period, since the greater the amount of water released by the contact lens, the greater the variation in the dimensions thereof, with potential negative repercussions on its optical properties.

A second known solution is provided by the use of external solutions, known generically and overall as "lachrymal substitutes" ("artificial tears"). These latter are aqueous solutions comprising substances, generally polymers, the overall properties of which tend to reproduce, as far as possible, the properties of the natural lachrymal liquid.

In order that an aqueous solution can be defined as a lachrymal substitute, it must possess particular chemico-physical and rheological characteristics and bio-compatibility. In particular, specific and high visco-elastic and hydrophilic properties are required, as well as muco-adhesive properties (in order to remain attached for as long as possible to the mucinic component of the lachrymal film), mucomimetic properties (for simulating in the best possible manner the behaviour of the lachrymal film) and the ability to bathe the cornea, in addition, obviously, to general compatibility with the tissues of the eye.

The use of lachrymal substitutes provides for their addition as drops directly on to the eye to which the contact lens is fitted, so that the need to have recourse to this expedient is a not very pleasing eventuality to many people, without considering the further inconvenience of having to carry phials or containers with one. Moreover, the beneficial effect of the lachrymal substitutes is very limited over time, so that it is often necessary to have recourse to them several times a day and in all kinds of places.

In certain cases, provision is also made for the application of the lachrymal substitute to take place directly on the lens, both when worn and prior to its being fitted, but this expedient does not substantially modify the to picture described above. In fact, the absorption of the lachrymal substitute into the lens is limited to its outermost surface layers, and is therefore retained in very small amounts and thus with a beneficial effect necessarily limited over time.

The wider view of the technical field of reference of the invention is completed by contact lenses used as vehicles for the administration through the eye of drugs for therapeutic use. Such lenses, known also as "ophthalmic dressings", are typically contact lenses obtained in a quite conventional manner, to which are then added one or more drops of the drug to be administered. The effect of release of the drug has, however, a very limited duration. Some solutions for contact lenses are also known for use as ophthalmic dressings, in which an endeavour has been made to increase the duration of the release of the drug. One of these solutions provides for the interposition of a support soaked in the substance to be administered between a pair of contact lenses.

DESCRIPTION OF THE INVENTION

The problem underlying the present invention is that of providing a contact lens, a method for producing same, and also a pack for the storage and maintenance of contact lenses structurally and functionally designed to remedy the limits described above with reference to the prior art cited.

This problem is solved by the present invention by means of a contact lens, a method for producing same, and a pack for its storage and maintenance, provided in accordance with the following claims.

BRIEF DESCRIPTION OF THE DRAWINGS

The characteristics of the invention will become clearer from the following detailed description of a preferred exemplary embodiment thereof, illustrated by way of non-limiting example with reference to the appended drawings, in which.

PREFERRED WAY OF IMPLEMENTING THE INVENTION

In the appended drawings, a contact lens produced according to the present invention is designated as a whole by 4.

The contact lens 4 is a lens of the soft type and may be of any known type, for cosmetic or corrective use, coloured or transparent, without thereby influencing to any significant extent the innovative aspects of the present invention.

The lens 4 is produced according to the following method.

In a first step, according to techniques that are quite conventional per se (by moulding or turning), a dry semi-manufactured product of polymeric material is produced, capable of imparting to the lens the structure and final configuration. The dry semi-manufactured product may be obtained from a polymeric mixture based on HEMA or from any other polymer or copolymer suitable for this purpose and normally used in the field.

In a subsequent preparation step, the dry semi-manufactured product is then hydrated by immersion in an aqueous solution, suitably agitated, so that into the solid component a liquid component is substantially uniformly absorbed, which favours comfortable use of the lens and therefore its compatibility with the eye of a user in which it is intended to be worn.

At the end of the hydration step, the lens 4 is then ready to be packaged and afterwards sterilised by means of treatment in an autoclave at around 120° C. for a period of around 20 minutes.

Figure 1:
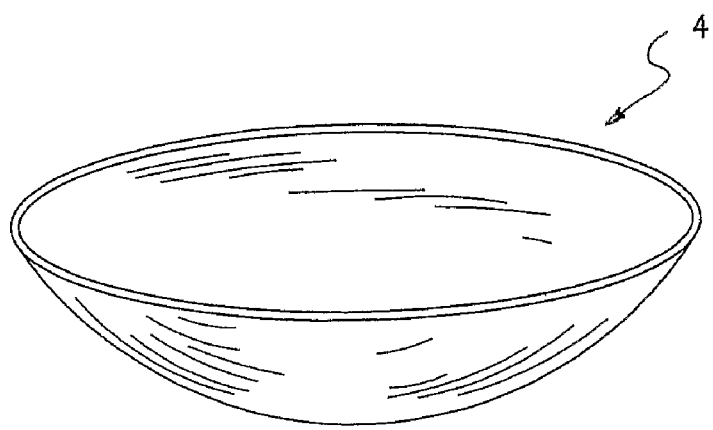
FIG. 1 is a diagrammatic perspective view of a contact lens produced according to the present invention.
Figure 2:
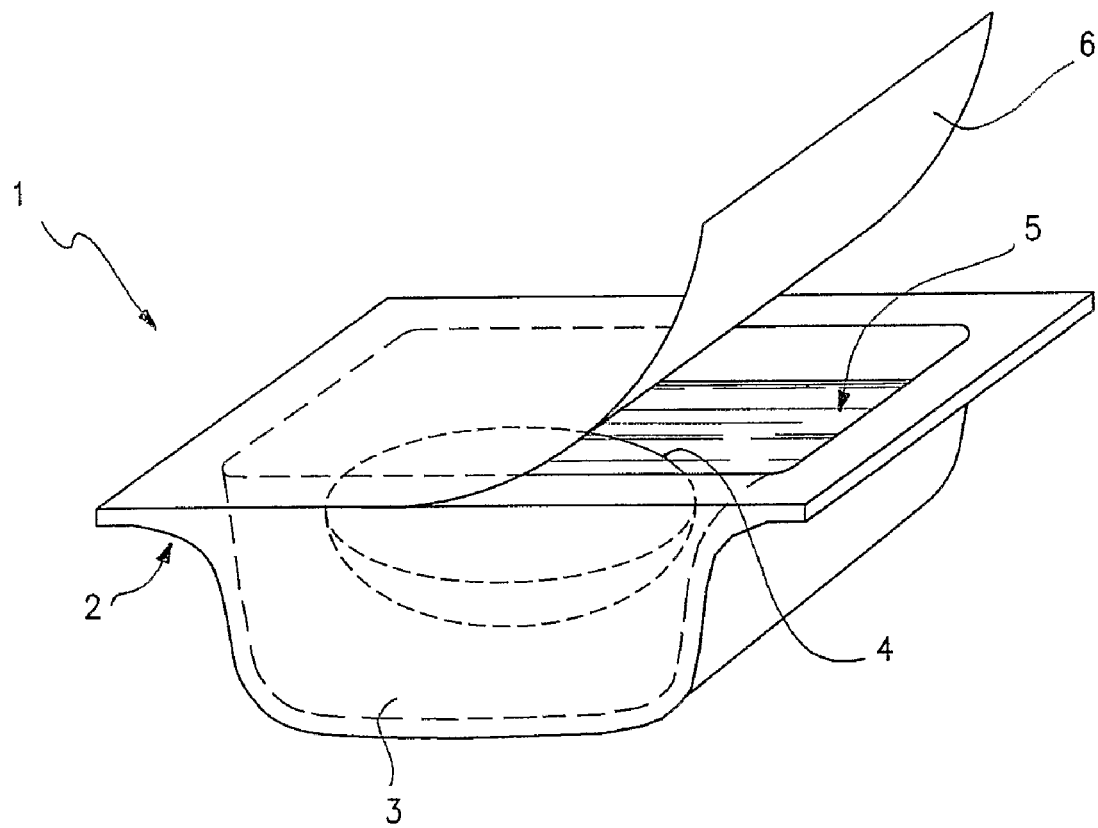
FIG. 2 is a diagrammatic perspective view of a pack for the storage and maintenance of the contact lens of FIG. 1.

FIG. 2 illustrates a pack for the storage and maintenance of the lens 4, indicated as a whole by 1. The pack 1 comprises a support 2, sheet-like and made for example of plastics material, configured in such a way as to define a container 3, inside which the lens 4 is immersed in a maintenance liquid 5.

The pack 1 also comprises a membrane 6 (so-called foil) coupled, for example by means of heat-welding, on a peripheral edge of the support 2 so as to seal the container 3 and prevent the escape of the lens 4 or of the liquid 5. The coupling between membrane 6 and support 2 is effected in such a way as to guarantee the closure of the container 3, permitting at the same time its manual removal by the user on deciding to extract the lens from the pack 1.

For greater clarity, in FIG. 2, the membrane 6 is shown in a partially lifted position.

According to a first aspect of the invention, the aqueous solution in which the dry semi-manufactured product is immersed for the hydration treatment is a solution capable of being used as a lachrymal substitute.

The contact lens thus obtained therefore comprises, like a conventional lens, a solid component, composed substantially of the polymeric material, and a liquid component distributed substantially uniformly in the solid component in which the liquid component is a lachrymal substitute.

The fraction of liquid component present in the contact lens is between 25% and 75%.

The lachrymal substitute used in the present invention is constituted by an aqueous solution comprising an effective amount of one or more polymers selected from the group consisting of polyvinyl alcohols and their derivatives, polysaccharides and their derivatives, and also cellulose derivatives. Preferably, the lachrymal substitute comprises, in addition to one or more polymers identified above, an effective amount of metallic ions, usually present also in natural lachrymal liquid, such as calcium, potassium and/or magnesium ions.

The polymers present in the lachrymal substitute may have a linear, branched or crosslinked structure, preferably such as to reproduce and simulate the structure of the mucinic cells present in natural lachrymal liquid.

In particular, the preferred lachrymal substitutes comprise polysaccharides and their derivatives, such as, for example, dextran, galactoxyloglucan, hyaluronic acid or their derivatives.

In an absolutely preferred manner, the lachrymal substitute comprises an effective amount of a galactoxyloglucan extracted from to tamarind seed (TSP). This polysaccharide has a molecular weight of around 600 KDalton, optimum hydrophilic properties and a branched molecular structure which renders it particularly similar to the natural mucinic cells and therefore able to bond effectively with the proteins of the mucous layer.

TSP also has other characteristics which cause it to be particularly preferred among the other compounds used as active principles in lachrymal substitutes.

A first of these characteristics is provided by its considerable heat resistance, which allows TSP to resist, without altering significantly, the conditions for sterilization of the lens in an autoclave (around 120° C. for about 20 minutes).

A second advantageous characteristic is provided by the capacity of TSP for blocking ultraviolet radiation (UV), which makes it possible to save an additive commonly used in contact lenses. Not only this, the slow and gradual release of the TSP-based solution in the eye allows protection from UV rays on an ocular surface greater than that strictly covered by the lens.

A third characteristic exhibited by the TSP-based lachrymal substitutes when used in a contact lens according to the present invention lies in the fact that, surprisingly, their behaviour within the polymer constituting the solid component is, in terms of swelling of the latter, entirely comparable to that of a normal physiological solution, imparting in the hydration phase substantially the same variations to the dry semi-manufactured product both in the radial direction and in the linear direction. This makes it possible to maintain substantially unvaried the parameters currently in use for the sizing of the dry semi-manufactured product. According to various studies, other common lachrymal substitutes tend to swell the more common polymeric material (HEMA) in a different manner from the physiological solution, such that their use as liquid component of the lens according to the present invention involves revision of the sizing of the dry semi-manufactured product and therefore of the machining process.

A fourth characteristic, particularly significant in the application of TSP in a lens according to the present invention, is provided by its optimum capacity, entirely unexpected, of remaining for a long time within the polymer constituting the solid component of the contact lens 4. This property allows the lens 4 to retain the lachrymal substitute for a substantially longer period within the solid component, so as to prolong the beneficial effect thereof.

The TSP-based aqueous solution may comprise from 0.1% to 1% by weight of TSP, and preferably comprises 0.2% thereof. In addition to the TSP, the solution may also comprise a buffering agent and a disinfecting agent.

A second lachrymal substitute that can be used for the production of contact lenses according to the present invention is constituted by an aqueous solution comprising an effective amount of sodium hyaluronate. In particular, the aqueous solution may comprise sodium hyaluronate in an amount of between 0.1% and 0.3% by weight, preferably around 0.2%, a surfactant, for example in an amount of around 0.0015%, a disinfecting agent, for example disodium EDTA, in an amount of around 0.1%, a buffering agent such as to maintain an overall pH of around 7.3-7.4, and also, optionally, sodium chloride in an amount of around 0.9%.

Owing to the presence of the lachrymal substitute in its liquid component, the fitting of the contact lens according to the invention is much more comfortable, significantly reducing the problems of a sensation of ocular dryness normally deriving from the use of conventional contact lenses.

The lachrymal substitute, in fact, is slowly released into the eye, developing a lubricating, hydrating and re-epithelising action which restores the lachrymal film, thus preventing, or at least greatly limiting, the occurrence of the problems of ocular dryness.

It has further been found that the speed of release of the lachrymal substitute depends on the temperature, determining a greater speed of release when the lens is worn by the user (to which an internal temperature of around 35° C. may be attributed), compared with when the lens is kept in the appropriate containers (temperature normally between 18° C. and 25° C.).

The contact lenses according to the invention may be produced so as to have to be replaced monthly or more frequently, for example daily, weekly or twice-weekly, depending on the polymeric material preselected and on its characteristics of retention of the liquid component.

Preferably, the contact lens is of the weekly or daily replacement type.

EXAMPLE 1

A soft contact lens was produced from a dry semi-manufactured product obtained by moulding from a polymeric mixture based on HEMA, and which was then hydrated in an aqueous solution comprising 0.2% of TSP, around 2% of mannitol and around 2% of monobasic and dibasic sodium phosphate.

EXAMPLE 2

A soft contact lens was produced by hydrating a dry semi-manufactured product, obtained in an analogous manner to that of example 1, in an aqueous solution comprising 0.2% of sodium hyaluronate, around 0.0015% of a surfactant, 0.1% of disodium EDTA as disinfecting agent, and a buffering agent based on sodium phosphate.

The contact lenses obtained from examples 1 and 2 were then subjected to some tests.

As a preliminary, the distribution of the lachrymal substitute within the lens was evaluated. These preliminary analyses were conducted by sectioning the lens into a representative number of samples, coloration with suitable dyes reacting with the hyaluronate and the TSP (for example saframin and toluidine blue) and subsequent observation of the intensity of the coloration with an optical microscope.

These analyses showed that the lenses obtained according to example 1 and example 2 exhibit a substantially uniform distribution of sodium hyaluronate and TSP within the lens, over its entire thickness.

The lenses of examples 1 and 2 were then tested on various subjects in order to check the wearability and the degree of comfort during use compared with conventional lenses, hydrated with physiological solution.

Both the contact lenses tested provided good results in terms of comfort of fitting on the eye and of duration of time before the onset of the first symptoms of ocular dryness, far better than those obtained by the conventional contact lenses.

The tests also showed that the lens hydrated with the TSP-based lachrymal substitute (example 1) is more effective than that obtained with the lachrymal substitute based on sodium hyaluronate (example 2), maintaining its capacity for preventing ocular dryness for a longer time.

According to another aspect of the present invention, the maintenance liquid 5 in which the lens 4 is immersed in the pack 1 is also a lachrymal substitute and, preferably, is of the same type as the lachrymal substitute used in the step of hydration of the dry semi-manufactured product.

In this way, the possibility is avoided of loss of lachrymal substitute present in the contact lens, though in any case limited to the outermost surface layers, because of substitution with a less suitable maintenance liquid, for example the usual physiological solution.

According to another aspect of the present invention, the packaging of a soft contact lens using as maintenance liquid a solution capable of being used as a lachrymal substitute may also be applied to soft contact lenses of conventional type, hydrated with physiological solution.

In this case, in fact, the immersion of the finished contact lens in a maintenance liquid based on a lachrymal substitute means that at the outermost surface layers of the lens, owing to the normal process of exchange with the actual inner liquid component, some fraction of lachrymal substitute is absorbed. In this way, when the lens is extracted from the container of the pack 1 in order to be worn by a user, it has, at least in its outermost layers, an amount of lachrymal substitute sufficient to ensure more comfortable use thereof, even for many hours, compared with the conventional lenses hydrated and maintained in physiological solution.

The duration of the beneficial effect will certainly be limited with respect to the case described previously in which the lens is hydrated with a lachrymal substitute, yet it is not insignificant.

In a particularly preferred manner, the lachrymal substitute used as maintenance liquid in a pack for the storage and maintenance of a contact lens of conventional type, that is, hydrated with physiological solution, is based on TSP. Owing, in fact, to the surprising and unexpected affinity of same with the polymer constituting the solid component of the lens, the beneficial effect deriving from its presence on the surface of the lens once removed from the pack in order to be fitted onto the eye, persists for a decidedly longer time compared with the other lachrymal substitutes.

Preferably, the contact lens will be of the frequent replacement type, for example weekly or more frequently, and, even more preferably, in order to benefit fully from the advantages offered by this aspect of the invention, the contact lens will be of the disposable type, for daily replacement.

According to a further aspect of the invention, provision is also made for the possibility of preserving and optionally disinfecting the contact lenses obtained according to the present invention with a preserving solution. Solutions of this type are used for preserving the lenses between one application and another, once removed from the storage and maintenance pack in which they are sold.

Preferably, the preserving solution comprises an effective amount of the polymer already present in the liquid component of the contact lens.

For example, in the case of a preserving solution for a contact lens comprising a TSP-based lachrymal substitute, such a preserving solution for the contact lenses will comprise a buffered physiological solution and an effective amount of TSP.

Optionally, provision is made for the preserving solution to be able to have disinfectant properties, so that it may also comprise a disinfecting agent from among those normally used in the field, for example sodium EDTA.

The presence in the preserving solution for the contact lenses of the polymer which is the basis of the lachrymal substitute in which the lens itself is soaked, makes it possible, particularly in the case of lenses with a low, for example monthly, frequency of replacement, to prolong over time the efficiency of the contact lens according to the invention. In fact, with use, the lachrymal substitute present initially in the lens will tend to decrease and its preservation in a solution such as that described above makes it possible, at least partially, to maintain in the lens an acceptable amount of the polymer which is the basis of the lachrymal substitute, prolonging its beneficial effect.

As in the case relating to the packaging of the contact lenses, this solution for preserving the contact lenses may also be used for contact lenses obtained in a conventional manner.

The present invention therefore solves the problem mentioned above with reference to the prior art cited, offering at the same time numerous other advantages, including the fact of providing a contact lens which may be obtained by means of a simple and inexpensive production method. A further advantage of the invention is provided by the fact that the wearability of the contact lens is increased significantly, thus making it particularly useful for use in notoriously unfavourable conditions, for example in work stations in front of monitors or television screens.

The invention claimed is:

1. A soft contact lens comprising a solid component capable of imparting shape and structure to said lens and a liquid component distributed substantially uniformly in said solid component, capable of favoring the compatibility between said lens and the eye of a user of said lens, wherein said liquid component comprises an aqueous solution used as a lachrymal substitute.

2. A soft contact lens according to claim 1, wherein said aqueous solution comprises an effective amount of one or more polymers selected from the group consisting of polyvinyl alcohols and their derivatives, polysaccharides and their derivatives and cellulose derivatives.

3. A soft contact lens according to claim 2, wherein said aqueous solution comprises an effective amount of dextran, or galactoxyloglucan or hyaluronic acid or their respective derivatives.

4. A soft contact lens according to claim 3, wherein said aqueous solution comprises an effective amount of galactoxyloglucan extracted from tamarind seed.

5. A soft contact lens according to claim 4, wherein said galactoxyloglucan extracted from tamarind seed is present in an amount of between 0.1% and 1%, preferably around 0.2%.

6. A soft contact lens according to claim 3, wherein said aqueous solution comprises an effective amount of sodium hyaluronate.

7. A soft contact lens according to claim 6, wherein said sodium hyaluronate is present in an amount of between 0.1% and 0.3%.

8. A soft contact lens according to claim 1, wherein said aqueous solution comprises an effective amount of one or more metallic ions selected from magnesium, calcium or potassium ions.

9. A soft contact lens according to claim 1, arranged to be replaced monthly or more frequently.

10. A soft contact lens according to claim 9, arranged to be replaced weekly or daily.

11. A pack for the storage and maintenance of contact lenses, comprising a support defining at least one container in which is contained a maintenance liquid and a soft contact lens immersed in said maintenance liquid wherein said soft contact lens is according to claim 1 and that said maintenance liquid is a solution capable of being used as a lachrymal substitute.

12. A pack according to claim 11, wherein said maintenance liquid has substantially the same composition as the aqueous solution constituting the liquid component of said contact lens.

13. A method for producing a soft contact lens comprising the steps of:
   a. obtaining a dry semi-manufactured product of said lens, made of polymeric material, constituting a solid component of said lens,
   b. hydration of said dry semi-manufactured product in an aqueous solution to impart a liquid component distributed substantially uniformly in said solid component and thus obtain said contact lens,
   wherein said aqueous solution is used as a lachrymal substitute.

14. A method according to claim 13, wherein said aqueous solution comprises an effective amount of one or more polymers selected from the group consisting of polyvinyl alcohols and their derivatives, polysaccharides and their derivatives and cellulose derivatives.

15. A method according to claim 14, wherein said aqueous solution comprises an effective amount of dextran, or galactoxyloglucan or hyaluronic acid or their respective derivatives.

16. A method according to claim 15, wherein said aqueous solution comprises an effective amount of galactoxyloglucan extracted from tamarind seed.

17. A method according to claim 16, wherein said galactoxyloglucan extracted from tamarind seed is present in an amount of between 0.1% and 1%, preferably around 0.2%.

18. A method according to claim 15, wherein said aqueous solution comprises an effective amount of sodium hyaluronate.

19. A method according to claim 18, wherein said sodium hyaluronate is present in an amount of between 0.1% and 0.3%.

20. A method according to claim 13, wherein said lachrymal substitute comprises an effective amount of one or more metallic ions selected from magnesium, calcium or potassium ions.

21. A method according to claim 13, wherein said contact lens, after said hydration treatment, is subjected to sterilization within a container containing said lachrymal substitute.

* * * * *